(12) United States Patent
Scherl et al.

(10) Patent No.: US 8,168,161 B2
(45) Date of Patent: May 1, 2012

(54) METHOD TO PROMOTE ORAL HEALTH IN COMPANION ANIMALS

(75) Inventors: Dale Scherl, Lawrence, KS (US); Ellen Logan, Wamego, KS (US); Kathy Gross, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 1631 days.

(21) Appl. No.: 11/020,449

(22) Filed: Dec. 22, 2004

(65) Prior Publication Data

US 2006/0134014 A1 Jun. 22, 2006

(51) Int. Cl.
*A61K 8/00* (2006.01)
*A61K 31/355* (2006.01)
*A61K 31/34* (2006.01)

(52) U.S. Cl. .......................... 424/49; 514/458; 514/474

(58) Field of Classification Search .................... 424/49; 514/458, 474
See application file for complete search history.

(56) References Cited

U.S. PATENT DOCUMENTS

| | | | | |
|---|---|---|---|---|
| 4,272,512 A | 6/1981 | Gaffar | | 424/49 |
| 5,032,384 A | 7/1991 | Yeh et al. | | 424/49 |
| 5,141,755 A * | 8/1992 | Weisman | | 426/42 |
| 5,339,771 A | 8/1994 | Axelrod | | 119/710 |
| 5,376,374 A | 12/1994 | Zelaya | | 424/195.1 |
| 5,419,283 A | 5/1995 | Leo | | 119/709 |
| 5,460,802 A * | 10/1995 | Asami et al. | | 424/49 |
| 5,621,117 A | 4/1997 | Bethge et al. | | 549/39 |
| 6,503,483 B2 | 1/2003 | Shuch et al. | | 424/49 |
| 6,584,938 B2 * | 7/2003 | Sherrill et al. | | 119/710 |
| 6,746,681 B1 * | 6/2004 | Carroll | | 424/401 |
| 6,887,493 B2 * | 5/2005 | Shefer et al. | | 424/490 |
| 2002/0137728 A1* | 9/2002 | Montgomery | | 514/99 |
| 2005/0158252 A1* | 7/2005 | Romanowski et al. | | 424/49 |

FOREIGN PATENT DOCUMENTS

GB 2080681 A * 2/1982
WO WO 0187229 A2 * 11/2001

OTHER PUBLICATIONS

Petelin et al., "Local delivery of liposome-encapsulated superoxide dismutase and catalase suppress periodontal inflammation in beagles", Journal of Clinical Periodontology, vol. 27, No. 12, pp. 918 (2000).*
Hill's Pet Nutrition: Canine Oral Care Adult Pet Food and Feline Oral Care Adult Pet Food. (2007).*
Hill's Pet Nutrition Timeline. www.hillspet.com/hillspet/ourCompany/heritage/HillsTimeline (2008).*
Battino, M. et al. (1999) *Crit. Rev. Oral Biol. Med.* 10(4), 458-476.
Clarke, D.E. (2001) *J. Vet. Dent.* 18(4), 177-183.
Cohen, R.E. et al. (1991) *Clin. Prev. Dent.* 13(5), 20-24.
Leggott, P.J. et al. (1986) *J. Periodontol.* 57(8), 480-485.
Vogel, R.I. et al. (1986) *J. Periodontol.* 57(8), 472-479.

* cited by examiner

*Primary Examiner* — Kevin E Weddington
(74) *Attorney, Agent, or Firm* — Shannon McGarrah

(57) ABSTRACT

A method for promoting oral health in a companion animal comprises causing the animal to ingest a composition comprising an oral health-promoting effective total amount of at least one antioxidant.

17 Claims, No Drawings

METHOD TO PROMOTE ORAL HEALTH IN COMPANION ANIMALS

FIELD OF THE INVENTION

The present invention relates to a method of promoting oral health in a companion animal.

BACKGROUND OF THE INVENTION

Companion animals such as cats and dogs require oral care. Poor oral health can cause animals pain and serious dental problems throughout life, as well as possibly lead to more serious illnesses, such as, for example, heart and kidney disease. According to the American Veterinary Dental Society and leading veterinary dental specialists, 70% of cats and 80% of dogs have some form of gum disease by age 3. Unhealthy gums, including gingival inflammation or gingivitis, are considered to be a common oral health issue affecting companion animals.

U.S. Pat. No. 6,503,483 describes compositions and methods for treatment of gum disease in humans and animals by topical administration of an orally absorbable dental formulation comprising vitamin C.

U.S. Pat. No. 5,376,374 proposes alleviation of gum disease by administration of an oral rinse composition and dietary supplementation with minerals and vitamins including vitamins C and E.

U.S. Pat. No. 5,032,384 describes compositions and methods for treatment of periodontal disease using a combination of an arylpropionic nonsteroidal anti-inflammatory drug (NSAID) and an antioxidant.

U.S. Pat. No. 4,272,512 proposes topical use of oral compositions and methods for inhibiting symptoms of gingivitis using tranexamic acid and folic acid.

Battino et al. (1999) *Crit. Rev. Oral Biol. Med.* 10(4), 458, review possible therapeutic effects of antioxidants in treating or preventing inflammatory periodontal disease.

Clarke (2001) *J. Vet. Dent.* 19(4), 177, proposes topical use of zinc ascorbate gel as an oral antiseptic to improve feline oral health.

Despite the availability of oral care products for companion animals, providing proper oral care to a companion animal remains a challenge due to, among other things, inconvenience, inadequateness, difficulty, and expense. For example, routine veterinary dental examinations and cleaning can be expensive. Regular brushing by the animal owner, though beneficial, can be an inconvenient chore that is difficult to perform or carry out on a regular basis. Conventional hard, crunchy dry foods, chew toys, and the like, fail to remove plaque and tartar at the gumline and are inadequate to promote periodontal health. There remains, therefore, a need for convenient and effective methods of promoting oral health in companion animals.

SUMMARY OF THE INVENTION

There is now provided a method of promoting oral health in a companion animal. The method comprises causing the animal to ingest a composition comprising at least one antioxidant in an oral health-promoting effective total antioxidant amount.

In some embodiments, the animal is a canine.
In other embodiments, the animal is a feline.
In some embodiments, the method comprises causing the animal to ingest a composition comprising an oral health-promoting effective total amount of vitamin C, vitamin E or a combination thereof.

Advantages and benefits of the present invention will be apparent to one skilled in the art from reading this specification.

DETAILED DESCRIPTION

It has been found in accordance with this invention that ingested antioxidants can be surprisingly effective in promoting oral health in animals. Without being held to a particular theory, it is believed that free radicals, as well as oxidative processes, are involved in the processes of inflammation. For example, cyclooxygenase enzymes provide an oxygenation step in conversion of arachidonic acid to the pro-inflammatory molecule prostaglandin E2. Reactive oxygen species such as, for example, nitric oxide are contributors to inflammatory processes. Antioxidants are believed to inhibit the inflammatory processes that cause, for example, gingival inflammation, gingivitis or periodontal disease.

In various embodiments, the present invention provides methods of promoting oral health in a companion animal, such methods comprising causing the animal to ingest a composition comprising at least one antioxidant in an oral health-promoting effective total antioxidant amount, and optionally additional ingredients.

The term "oral health" herein refers to any oral condition involving the teeth and/or gums. In one embodiment, the method of the invention is used to promote gum and/or periodontal health. The expression "oral health-promoting", therefore, can include mitigation, prevention, or treatment of oral conditions associated with the gums and/or tissues/structures surrounding and supporting the teeth. Non-limiting examples of oral conditions contemplated herein include gingivitis (inflammation of the gums (gingival tissue)) and periodontitis (inflammation and/or infection present both in the gingiva and in the connective tissue which supports the teeth).

In one embodiment, the method is effective to reduce accumulation of plaque. However, in other embodiments the method is effective to promote gingival and/or periodontal health even where plaque accumulation is not inhibited. It is particularly surprising that practice of the present method can, as illustratively shown in Example 1 hereinbelow, keep gingivitis at a low baseline level even as plaque, normally a factor promoting gingivitis, accumulates.

It is contemplated that the methods of the present invention may be useful for a variety of animals such as companion animals (e.g., canine, feline), primates (e.g., monkey, baboon), ruminant animals (e.g., cow, sheep, goat, horse), or rodents (e.g., mouse, rat, guinea pig). In particular, the present methods are useful for companion animals such as cats and dogs.

The methods of this invention contemplate administration of any of a variety of compositions comprising the one or more antioxidants to the animal. Contemplated compositions suitable for ingestion by a companion animal include, for example, foods, supplements, treats, snacks and toys (typically chewable and consumable toys).

In one embodiment, the composition comprising the one or more antioxidants can be fed to the animal as a component of its food intake. The food intake of the animal can meet its ordinary nutritional requirements, which a skilled artisan can determine based upon the animal's species, age, sex, weight, and other factors. For example, a typical diet for a canine of 1-6 years of age contains on a dry matter basis about 23% protein, about 15% fat, about 0.6% phosphorus, 0.6% calcium and about 0.3% sodium; and, for older canines and felines, a typical diet can be, for example, as provided in Table 1.

TABLE 1

Typical composition of diet for older canines and felines

| Component | Canine | Feline |
|---|---|---|
| crude protein (% dry matter) | 15-25 | 26-50 |
| crude fat (% dry matter) | 7-20 | 10-30 |
| crude fiber (% dry matter) | >2 | <10 |
| calcium (% dry matter) | 0.5-1.2 | 0.6-1.5 |
| phosphorus (% dry matter) | 0.25-1.2 | 0.5-1.5 |
| sodium (% dry matter) | 0.15-0.5 | 0.15-0.5 |
| magnesium (% dry matter) | 0.05-0.2 | 0.05-0.15 |
| energy density [1] | 3.0-4.5 | 3.5-5.0 |

[1] kcal ME (metabolizable energy) per kg food (dry matter)

In another embodiment, the composition is a food supplement comprising the one or more antioxidants. Supplements include, for example, a feed or pet food used with another feed or pet food to improve the nutritive balance or performance of the total. Contemplated supplements include compositions that are fed undiluted as a supplement to other feeds or pet foods, offered free choice with other parts of an animal's ration that are separately available, or diluted and mixed with an animal's regular feed or pet food to produce a complete feed or pet food. AAFCO, for example, provides a discussion relating to supplements in the American Feed Control Officials, Inc. Official Publication, p. 220 (2003). Supplements can be in various forms including, for example, powders, liquids, syrups, pills, encapsulated compositions, etc.

In another embodiment, the composition is a treat comprising one or more antioxidants. Treats include, for example, compositions that are given to an animal to entice the animal to eat during a non-meal time. Contemplated treats for canines include, for example, dog biscuits in the shape of dog bones. Treats can be nutritional, wherein the composition comprises one or more nutrients, and can, for example, have a composition as described above for food. Non-nutritional treats encompass any other treats that are non-toxic. The one or more antioxidants, for example, can be coated onto the treat, incorporated into the treat, or both.

In another embodiment, the composition is a toy comprising the one or more antioxidants. Toys include, for example, chewable toys. Contemplated toys for dogs include, for example, artificial bones. The one or more antioxidants, for example, can be present in a coating on the surface of the toy or on the surface of a component of the toy, or can be incorporated partially or fully throughout the toy, or both. In a contemplated embodiment, the one or more antioxidants are orally accessible by the intended user.

Illustrative toys suitable for modification in accordance with the invention are disclosed in the documents individually cited below and incorporated herein by reference.

U.S. Pat. No. 5,339,771 and references disclosed therein.
U.S. Pat. No. 5,419,283 and references disclosed therein.

It should be recognized that this invention contemplates both partially consumable toys (e.g., toys comprising plastic components) and fully consumable toys (e.g., rawhides and various artificial bones). It should be further recognized that this invention contemplates toys for both human and non-human use, particularly for companion, farm, and zoo animal use, and particularly for dog or cat use.

The terms "treat" and "toy" can be considered interchangeable for the purposes of this specification. However, in general a treat is fully edible and a toy in accordance with the invention has an edible coating.

In preparing a composition of the present invention, the one or more antioxidants can, for example, be incorporated into the composition during formulation processing, such as during and/or after mixing of other components of the composition. Distribution of these components into the composition can be accomplished by any conventional method including standard mixing procedures.

Compositions of the present invention (particularly foods) can be prepared in a canned or wet form using conventional pet food processes. In one contemplated embodiment, ground animal (e.g., animal, poultry, and/or fish) proteinaceous tissues are mixed with other ingredients, including for example animal fats and vegetable oils, cereal grains, other nutritionally balancing ingredients, special purpose additives (e.g., vitamin and mineral mixtures, inorganic salts, cellulose and beet pulp, bulking agents, and the like); and water sufficient for processing is also added.

Compositions of the present invention (particularly foods) can be prepared in a dry form using conventional processes. In one contemplated embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which can include, for example, flavors, fats, oils, powders, and the like. Kibble also can be made from the dough using a baking process, rather than extrusion, wherein the dough is placed into a mold before dry-heat processing. Kibble also can be made from a food matrix undergoing pelletization. It is important to note that the at least one antioxidants can be incorporated into the food composition by adding the at least one antioxidants, for example, to the above-described mixtures before extrusion or by coating the extruded kibble or pellets with, for example, at least one antioxidants as an ingredient of a topical coating.

Treats of the present invention can be prepared by, for example, an extrusion or baking process similar to those described above for dry food. Other processes also can be used to either apply a coating comprising the one or more antioxidants on the exterior of existing treat forms, or inject the one or more antioxidants into an existing treat form.

Animal toys of the present invention are typically prepared by coating any existing toy with a composition comprising at least one antioxidant.

In various embodiments, methods for promoting oral health in the animal comprise causing the animal to ingest at least one antioxidant. An antioxidant is any material that either directly quenches a free radical or indirectly causes a free radical to become quenched. One skilled in the art knows that a variety of materials have free radical quenching or absorbing capacity. For example, the following are raw ingredients that are high in oxygen radical absorbing capacity ("ORAC") content: spinach, spinach pomace, tomato pomace, citrus pulp, grape pomace, carrot, carrot granules, broccoli, green tea, ginkgo biloba, corn gluten meal, algae, curcumin, astaxanthin, beta-carotene, glutathione, green tea, lutein, lycopene, N-acetylcysteine, polyphenols, soy isoflavones, S-adenosylmethionine, sulfur-containing amino acids, taurine, tocotrienols, folate, vitamin A, vitamin C and vitamin E.

As described above, the antioxidant or mixture of antioxidants can be fed to a animal as a component of its food or as a food supplement. The quantities provided in the food, all on a dry matter basis, are stated herein as the active material. The antioxidant amount should not exceed a maximum above which toxicity is brought about. Preferably, the antioxidant, or mixture thereof, is fed to the animal in a total amount effective to promote oral health. What constitutes an effective amount varies depending on the species of the animal, the type of antioxidant(s) and other factors. One of skill in the art will, by routine testing based on the disclosure herein, readily establish a total antioxidant amount having oral health-promoting effects in any particular situation.

In various embodiments, the antioxidant can be, for example, vitamin C, vitamin E, vitamin A, lipoic acid, astaxanthin, beta-carotene, L-carnitine, coenzyme Q10, glutathione, lycopene, lutein, N-acetylcysteine, soy isoflavones, S-adenosylmethionine, taurine, tocotrienols, spinach, tomato, citrus fruit, grape, carrot, broccoli, green tea, ginkgo biloba, corn gluten meal, rice bran, algae, curcumin, marine oil, fruits, vegetables, yeast, carotenoids, flavonoids, polyphenols, or mixtures thereof.

Examples of an antioxidant food, a food product, or a component thereof, raw or otherwise, include spinach (for example, spinach pomace), tomato (for example, tomato pomace), citrus fruit (for example, citrus pulp), grape (for example, grape pomace), carrot (for example, carrot granules), broccoli, green tea, ginkgo biloba, corn gluten meal, rice bran, algae, curcumin, marine oil, or yeast (for example, selenium yeast), or mixtures thereof.

In some embodiments, the antioxidant-comprising composition can comprise vitamin E, vitamin C, or both vitamin E and vitamin C.

Except where the context demands otherwise, the term "vitamin E" is used generically herein to encompass any tocopherol or tocotriene compound, including any enantiomer or racemate thereof, and any mixture of such compounds, having vitamin E activity, including α-tocopherol ((+)-2,5,7,8-tetramethyl-2-(4,8,12-trimethyltridecyl)-6-chromanol), β-tocopherol ((+)-2,5,8-trimethyl-2-(4,8,12-trimethyltridecyl)-6-chromanol), γ-tocopherol ((+)-2,7,8-trimethyl-2-(4,8,12-trimethyltridecyl)-6-chromanol), δ-tocopherol ((+)-8-methyl-2-(4,8,12-trimethyltridecyl)-6-chromanol), α-tocotrienol (2,5,7,8-tetramethyl-2-(4,8,12-trimethyl-3,7,11-tridecatrienyl)-6-chromanol) and β-tocotrienol (2,5,8-trimethyl-2-(4,8,12-trimethyl-3,7,11-tridecatrienyl)-6-chromanol). Vitamin E can be administered as any one or a mixture of the above compounds or in the form of various derivatives thereof such as esters, including vitamin E acetate, succinate, palmitate and the like, that exhibit vitamin E activity after ingestion by the animal. Typically vitamin E as used in the present method comprises α-tocopherol or an ester thereof.

In some embodiments, the vitamin E content of a composition can be at least about 100 ppm, illustratively about 100 to about 5000 ppm, about 250 to about 2500 ppm, or about 500 to about 1500 ppm.

Vitamin C can be administered as ascorbic acid, for example L-ascorbic acid, or as various derivatives thereof such as calcium phosphate salt, cholesteryl salt, and ascorbate-2-monophosphate. Salts of vitamin C include, for example, sodium salt, calcium salt, zinc salt and ferrous salt. Esters include, for example, stearate, palmitate and like derivatives. Vitamin C or a derivative thereof can be in any physical form, for example, a liquid, a semisolid, a solid, or a heat stable form that exhibits vitamin C activity after ingestion by the animal.

In some embodiments, the vitamin C content of a composition can be at least about 10 ppm, illustratively about 10 ppm to about 10,000 ppm, or about 20 to about 2000 ppm, or about 25 to about 500 ppm.

Lipoic acid can be administered as such, as a lipoate salt or ester, or as a lipoate derivative, for example as described in U.S. Pat. No. 5,621,117. As used herein, "lipoic acid" is synonymous with α-lipoic acid and can be provided in various forms including racemic mixtures, salts, esters and/or amides thereof.

Lipoic acid, if present in the composition, can be in an amount of at least about 100 ppm, at least about 50 ppm, or at least about 25 ppm, up to about 600 ppm or up to an amount which is not toxic to the animal.

L-carnitine can be present as L-carnitine or in a derivative form, for example, a salt (for example, hydrochloride), an ester (for example, fumarate ester or succinate ester), or as acetylated L-carnitine.

L-carnitine, if present in the composition, can be in an amount of at least about 500 ppm, at least about 200 ppm, at least about 100 ppm, or at least about 50 ppm. A non-toxic maximum quantity can be employed, for example, less than about 5,000 ppm.

Carotenoids can be present in the composition, including retinol (vitamin A), retinal, retinoic acid, α-carotene, β-carotene, γ-carotene, δ-carotene, lutein, lycopene, lycophyll, lycoxanthin, rhodoxanthin, astaxanthin and cryptoxanthin. Vitamin A can be present as vitamin A or derivatives such as $C_{2-20}$ fatty acid esters of vitamin A and the like.

Illustratively, β-carotene, if present in the composition, can be in an amount of about 1 to about 15 ppm.

Optionally, about 0.1 to about 5 ppm selenium can be used.

Optionally, at least about 1 ppm of lutein up to about 100 ppm or up to an amount which is not toxic to the animal can be used.

Optionally, at least about 25 ppm of coenzyme Q10 up to about 2000 ppm or up to an amount which is not toxic to the animal can be used.

Optionally, at least about 50 ppm of S-adenosylmethionine up to about 2000 ppm or up to an amount which is not toxic to the animal can be used.

Optionally, at least about 500 ppm of taurine up to about 5000 ppm or up to an amount which is not toxic to the animal can be used.

Optionally, at least about 25 ppm of soy isoflavone(s) up to about 5000 ppm or up to an amount which is not toxic to the animal can be used.

Optionally, at least about 50 ppm of N-acetylcysteine up to about 1000 ppm or up to an amount which is not toxic to the animal can be used.

Optionally, at least about 50 ppm of glutathione up to about 1000 ppm or up to an amount which is not toxic to the animal can be used.

Optionally, at least 50 ppm of *ginkgo biloba* extract up to about 1000 ppm or up to an amount which is not toxic to the animal can be used.

EXAMPLES

The following example is merely illustrative, and does not limit this disclosure in any way.

Example 1

This example illustrates that gingival inflammation does not increase in cats fed a nutritionally complete feline pet food supplemented with vitamins E and C in various combinations.

Thirty-eight cats were randomly assigned to one of the four groups A-D. A nutritionally complete feline pet food was supplemented with 4 different levels of the antioxidants vitamins C and vitamin E. The groups A-D are designated as follows:

| | |
|---|---|
| A | vitamin C - 35 ppm, vitamin E - 550 ppm |
| B | vitamin C - 35 ppm, vitamin E - 1000 ppm |
| C | vitamin C - 350 ppm, vitamin E - 550 ppm |
| D | vitamin C - 350 ppm, vitamin E - 1000 ppm |

Prior to study initiation, all cats received a complete dental cleaning including supragingival and subgingival plaque and tartar removal and polishing of all exposed tooth surfaces with rubber cup and pumice. Each cat received daily tooth brushing with a soft tooth brush and a pet dentifrice for a period of 5 days. Tooth brushing was discontinued 48 hours prior to baseline evaluations. At Day 0, all cats were evaluated for baseline plaque accumulation and gingival inflammation. Each cat was given a complete dental cleaning and four weeks later cats were again evaluated for plaque accumulation and gingival inflammation.

In a previous study using a similar model, cats were fed a typical dry grocery cat food having no vitamin C and 65 ppm vitamin E. This group of cats showed 142% increase in plaque and 52.4% increase in gingivitis over a 4 week period.

As shown in Table 2 below, there was no substantial change in the level of gingivitis from baseline over the four week period in groups A-D. This is in spite of the fact that each of groups A-D exhibited an increase from baseline values in level of plaque accumulation.

TABLE 2

Change over baseline in plaque and gingivitis scores

| | % change | |
|---|---|---|
| Group | plaque | gingivitis |
| A | 30.9 | −6.5 |
| B | 24.6 | 6.9 |
| C | 58.0 | −3.8 |
| D | 64.4 | −14.8 |

These data demonstrate that a feline pet food supplemented with various combinations of vitamins E and C can provide a protective effect, as indicated by no substantial change in level of inflammation, to gingival tissues over a four week time period.

All references cited above are incorporated herein by reference in their entirety.

The words "comprise", "comprises", and "comprising" are to be interpreted inclusively rather than exclusively.

What is claimed is:

1. A method for promoting oral health in a companion animal, the method comprising causing the animal to ingest a composition comprising at least one antioxidant in an oral health-promoting effective total antioxidant amount, wherein the at least one antioxidant is a combination of vitamin E and vitamin C and wherein the composition is in the form of a food.

2. The method of claim 1, wherein the animal is a canine.

3. The method of claim 1, wherein the animal is a feline.

4. A method for promoting oral health in a companion animal, the method comprising causing the animal to ingest a composition comprising at least one antioxidant in an oral health-promoting effective total antioxidant amount, wherein the at least one antioxidant is a combination of vitamin E and vitamin C, wherein the composition is in the form of a treat.

5. A method for promoting oral health in a companion animal, the method comprising causing the animal to ingest a composition comprising at least one antioxidant in an oral health-promoting effective total antioxidant amount, wherein the at least one antioxidant is a combination of vitamin E and vitamin C, wherein the composition is in the form of a toy coating.

6. The method of claim 1, wherein the at least one antioxidant is present in the composition in a total antioxidant amount effective for inhibition, or treatment of gingival or periodontal health.

7. The method of claim 6, wherein the total antioxidant amount is effective for mitigation, inhibition, or treatment of gingivitis.

8. The method of claim 1, wherein the composition comprises vitamin E in an amount of about 100 to about 5,000 ppm.

9. The method of claim 1, wherein the composition comprises vitamin E in an amount of about 250 to about 2,500 ppm.

10. The method of claim 1, wherein the composition comprises vitamin E in an amount of about 500 to about 1,500 ppm.

11. The method of claim 1, wherein the composition comprises vitamin C in an amount of about 10 to about 10,000 ppm.

12. The method of claim 1, wherein the composition comprises vitamin C in an amount of about 20 to about 2,000 ppm.

13. The method of claim 1, wherein the composition comprises vitamin C in an amount of about 25 to about 500 ppm.

14. The method of claim 4, wherein the at least one antioxidant is present in the composition in a total antioxidant amount effective for inhibition, or treatment of gingival or periodontal health.

15. The method of claim 14, wherein the total antioxidant amount is effective for mitigation, inhibition, or treatment of gingivitis.

16. The method of claim 5, wherein the at least one antioxidant is present in the composition in a total antioxidant amount effective for inhibition, or treatment of gingival or periodontal health.

17. The method of claim 16, wherein the total antioxidant amount is effective for mitigation, inhibition, or treatment of gingivitis.

* * * * *